(12) United States Patent
Mishima

(10) Patent No.: US 6,419,666 B1
(45) Date of Patent: Jul. 16, 2002

(54) ARTICLE FOR DEALING WITH BODY WASTES

(75) Inventor: Yoshitaka Mishima, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/606,030

(22) Filed: Jun. 29, 2000

(30) Foreign Application Priority Data

Jun. 29, 1999 (JP) .......................................... 11-183095

(51) Int. Cl.[7] ................................................ A61F 13/15
(52) U.S. Cl. ............................. 604/385.14; 604/385.28; 604/385.26; 604/385.01; 604/385.24
(58) Field of Search ........................ 604/385.01, 385.26, 604/385.28, 385.14, 358, 385.23, 385.21

(56) References Cited

U.S. PATENT DOCUMENTS

| | | | | |
|---|---|---|---|---|
| 3,532,093 A | * | 10/1970 | Lovret | 128/286 |
| 5,005,525 A | * | 4/1991 | Stanton | 119/95 |
| 5,062,840 A | * | 11/1991 | Holt et al. | 604/385.1 |
| 5,176,672 A | * | 1/1993 | Bruemmer et al. | 604/385.1 |
| 5,269,775 A | * | 12/1993 | Freeland et al. | 604/385.2 |
| 5,306,226 A | * | 4/1994 | Freeland | 604/385.1 |
| 5,344,516 A | | 9/1994 | Tanji et al. | |
| 5,576,091 A | * | 11/1996 | Zajaczkowski et al. | 428/192 |
| 5,752,946 A | * | 5/1998 | Boberg et al. | 604/385.2 |
| 5,792,130 A | * | 8/1998 | Widlund et al. | 604/385.1 |
| 5,814,037 A | * | 9/1998 | Coates | 604/393 |
| 6,077,254 A | * | 6/2000 | Silwanowicz et al. | 604/385.2 |
| 6,123,692 A | * | 9/2000 | Guidotti et al. | 604/385.1 |
| 6,133,501 A | * | 10/2000 | Hallock et al. | 604/369 |
| 6,152,907 A | * | 11/2000 | Widlund et al. | 604/385.08 |
| 6,168,583 B1 | * | 1/2001 | Tanji et al. | 604/385.14 |
| 6,248,098 B1 | * | 6/2001 | Sayama | 604/385.28 |

FOREIGN PATENT DOCUMENTS

| | | |
|---|---|---|
| GB | 2 329 842 | 4/1999 |
| JP | 6-178795 | 6/1994 |
| WO | 98/37839 | 9/1998 |

\* cited by examiner

*Primary Examiner*—John G. Weiss
*Assistant Examiner*—Jacqueline F Stephens
(74) *Attorney, Agent, or Firm*—Clark & Brody

(57) ABSTRACT

An article for dealing with body wastes including a panel which includes a topsheet, a backsheet and a core disposed therebetween has a bottom, a peripheral wall extending upward from a peripheral edge of the bottom and a top opening defined by the peripheral wall. The peripheral wall which is elastically stretchable along an edge of the opening includes an obtusely curved front peripheral wall section, an acutely curved a rear peripheral wall section and a pair of intermediate peripheral wall sections.

8 Claims, 7 Drawing Sheets

ARTICLE FOR DEALING WITH BODY WASTES

BACKGROUND OF THE INVENTION

This invention relates to an article for dealing with body wastes such as a feces-receiving pad, a urine-absorbent pad or an incontinence pad or the like.

Japanese Patent Application Disclosure Gazette No. 1994-178795 describes an absorbent article comprising a diaper cover longitudinally composed of front and rear waist regions and a crotch region extending between these two waist regions and provided along transversely opposite side edges of the diaper cover with a pair of holding flaps extending longitudinally of the diaper cover and biased to rise on the transversely side edges and a rectangular insertion pad made of absorbent material and placed on the upper surface of the diaper cover between the holding flaps.

The article described in the Japanese Patent Application Disclosure No. 1994-178795 enables the holding flaps of the pad to prevent leakage of an amount of body fluids from the pad. However, it is impossible for the pad itself to prevent leakage of body fluids.

SUMMARY OF THE INVENTION

It is an object of this invention to provide an article for dealing with body wastes functions not only to receive and absorb body wastes but also to prevent leakage of body wastes.

According to this invention, there is provided an article for dealing with body wastes comprising a laminated panel comprising a liquid-pervious topsheet, a liquid-impervious backsheet and a liquid-absorbent core disposed therebetween wherein the panel has a front region, a rear region and a third region extending therebetween, wherein:

the panel has a bottom, a peripheral wall extending upward from a peripheral edge of the bottom and surrounding the peripheral edge of the bottom and a top opening defined by the peripheral wall; and the peripheral wall has an elastic stretchability along an edge of the top opening and comprising an obtusely curved front peripheral wall section contouring the front region, a rear peripheral wall section curved more acutely than the front peripheral contouring the rear region and a pair of intermediate peripheral wall sections describing circular arcs convex outward transversely of the panel so as to contour the intermediate region.

The article for dealing with body wastes according to this invention can be used independently of the diaper cover by directly attaching the article to the shorts worn by a user.

The article for dealing with body wastes according to this invention may be attached to the cover member at a selectively appropriate position thereof depending on a particular purpose and thereby used as a feces-receiving pad, a urine absorbent pad or a sanitary napkin wherein body wastes received by the article through its top opening is absorbed by the core through the topsheet.

According to this invention, the bottom cooperates with the front and rear peripheral wall sections to form the pocket opening inward longitudinally of the panel while the bottom cooperates with the intermediate peripheral wall sections to form the pocket opening inward transversely of the panel. These pockets function to prevent an amount of body wastes from leaking beyond the peripheral edge of the panel's bottom.

DETAILED DESCRIPTION OF THE PREFERRED EMBODIMENTS

Details of an article for dealing with body wastes according to this invention will be more fully understood from the description of an absorbent pad adapted to be attached to the inner surface of a diaper cover as will be given hereunder with reference to the accompanying drawings.

Figure 1:
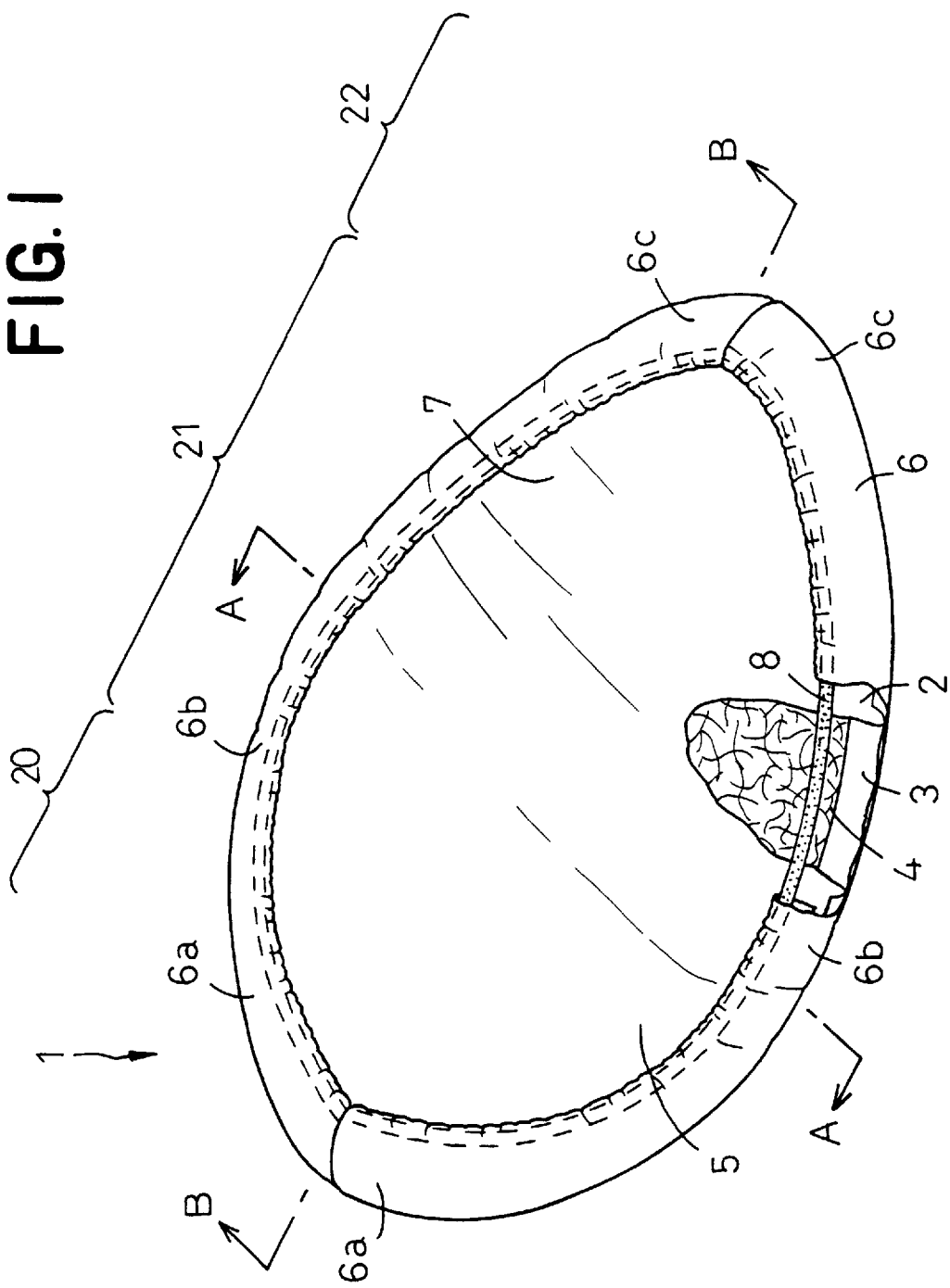
FIG. 1 is a partially cutaway perspective view showing a pad.

FIG. 1 is a partially perspective view showing an absorbent pad. The pad is provided in the form of a laminated panel 1 comprising a liquid-pervious topsheet 2, a liquid-impervious backsheet 3 and a liquid-absorbent core 4 disposed between these two sheets 2, 3 and joined to the inner surface of at least one of these two sheets 2, 3. Longitudinally, the panel 1 is composed of a front region 20, a rear region 22 and an intermediate region 21 extending between the front and rear regions 20, 22. As viewed in vertical direction, the panel 1 comprises an obovoid bottom 5, a peripheral wall 6 extending upward from a peripheral edge of the bottom 5 and surrounding the peripheral edge of the bottom 5 and an obovoid top opening defined by the peripheral wall 6. Within the top opening 7, the bottom 5 is exposed.

The peripheral wall 6 comprises an obtusely curved front peripheral wall section 6a, a rear peripheral wall section 6c curved more acutely than the front peripheral wall section 6a and a pair of intermediate peripheral wall sections 6b each describing a circular arc extending toward the upper surface of the bottom 5 in the intermediate region 21 of the panel 1. The peripheral wall 6 is provided along a peripheral edge of the top opening 7 with a film-like stretchable elastic member 8 secured under tension to the peripheral wall 6. In the panel 1, the peripheral wall 6 forms gathers along the peripheral edge of the top opening 7 as the elastic member 8 is contracted.

Figure 2:
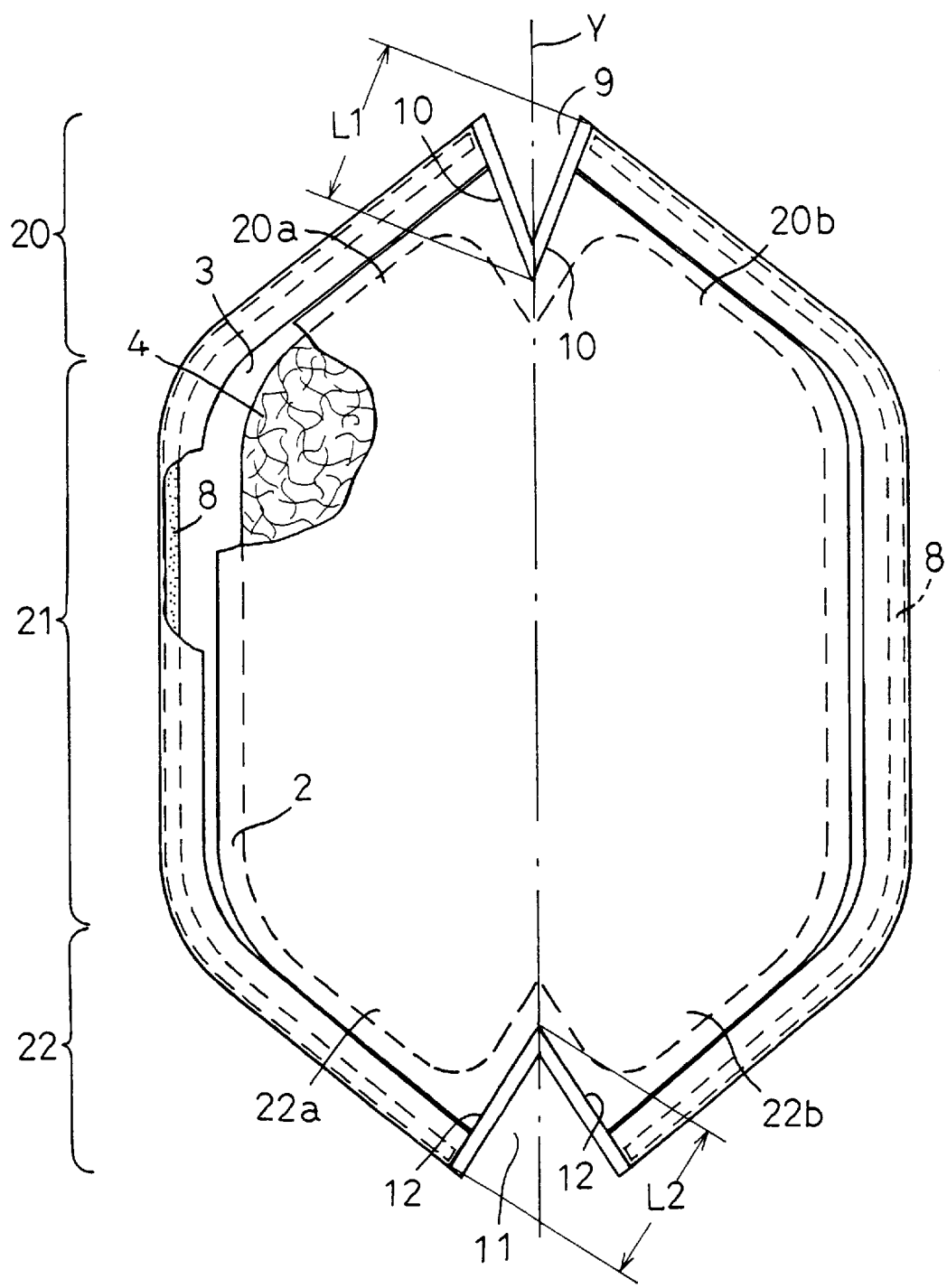
FIG. 2 is a partially cutaway plan view showing the pad of FIG. 1 before assembled.

FIG. 2 is a partially cutaway plan view showing the pad of FIG. 1 before assembled. In the panel 1, the core 4 overlies the backsheet 3 and the top sheet 2 overlies said core 4 to cover the latter.

The topsheet 2, the backsheet 3 and the core 4 have their outer edges respectively including a pair of sections extending in parallel to each other in the intermediate region 21 of the panel 1. Then these sections of the outer edge curve transversely inward from longitudinally opposite ends of the intermediate region 21 so that they may extend toward the front and rear ends of the panel 1 and progressively come nearer to a center line Y longitudinally extending to bisect a transverse dimension of the panel 1. The topsheet 2 and the core 4 have their areas smaller than that of the backsheet 3. The outer edge of the backsheet 3 is folded inwardly of the panel 1 to cover the elastic member 8.

Alternatively, in the intermediate region, the topsheet 2, the backsheet 3 and the core 4 may have their outer edges each including a pair of sections extending from the front end 20 toward the rear end 22 progressively nearer to the center line Y.

The panel 1 is formed on its front end 20 with a V-shaped notch 9 opening forward (i.e., upward as viewed in FIG. 2) longitudinally of the panel 1 around the center line Y. The topsheet 2 and the backsheet 3 are provided along legs of the notch 9 with first joining edges 10 progressively spaced from each other around the center line Y following the V-shape opening forward longitudinally of the panel 1.

Similarly, the panel 1 is formed on its rear end 22 with an inverted V-shaped notch 11 opening rearward (i.e., downward as viewed in FIG. 2) longitudinally of the panel 1 around the center line Y. An angle included by the notch 11 formed on the rear end 22 is larger than the angle included by the notch 9 formed on the front end 20. The topsheet 2 and the backsheet 3 are provided along legs of the notch 11 with second joining edges 12 progressively spaced from each other around the center line Y following the inverted V-shape opening rearward longitudinally of the panel 1. Each leg of the V-shape defined by the first joining edges 10 has a length designated by L1 and each leg of the inverted V-shape defined by the second joining edges 12 has a length designated by L2 wherein L1=L2. In the notches 9, 11, portions corresponding to the notches 9, 11 have been cut out from the topsheet 2, the backsheet 3 and the core 4.

To assemble the pad from the state illustrated by FIG. 2, respective divisions 20a, 20b of the front end 20 lying on both sides of the center line Y are drawn near to the center line Y and joined to each other along the first joining edges 10 on the center line Y. Similarly, respective divisions 22a, 22b of the rear end 22 are drawn near to the center line Y and joined to each other along the second joining edges 12 on the center line Y. Upon joining the divisions 20a, 20b and 22a, 22b together along the first and second joining edges 10, 12, respectively, the panel 1 is formed with the front, rear and intermediate peripheral wall sections 6a, 6c, 6b. In the panel 1 thus assembled, a peripheral length of the top opening 7 is smaller than a peripheral length of the bottom 5 and the peripheral wall 6 is therefore slant inwardly of the panel 1.

Figure 3:
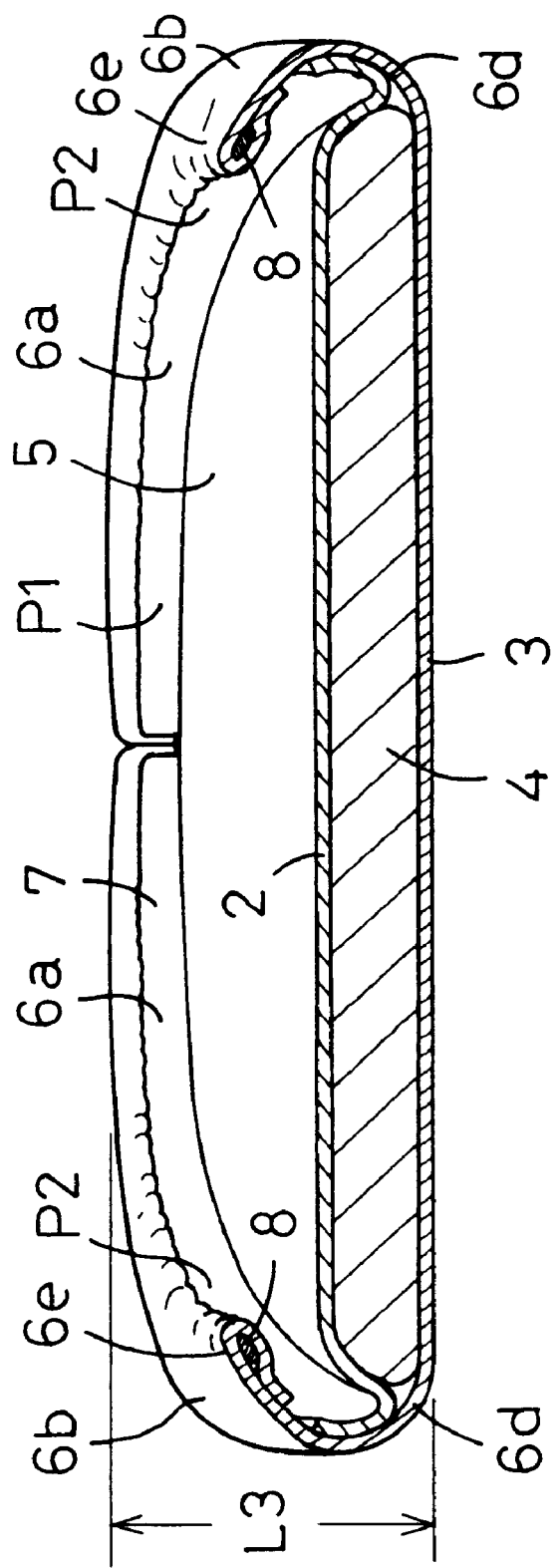
FIG. 3 is a sectional view taken along line A—A in FIG. 1.
Figure 4:
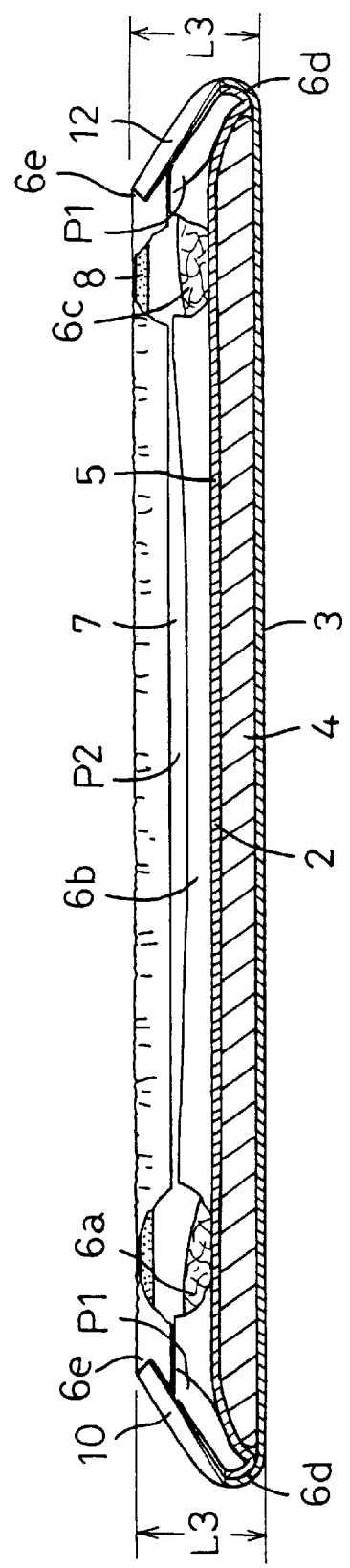
FIG. 4 is a sectional view taken along line B—B in FIG. 1.

FIGS. 3 and 4 are sectional views taken along lines A—A and B—B in FIG. 1, respectively. FIG. 4 shows the front and rear peripheral wall sections 6a, 6c partially cutaway. The front, rear and intermediate peripheral wall sections 6a, 6c, 6b curve upward to extend slightly beyond the bottom 5 of the panel 1. The front and rear peripheral wall sections 6a, 6c comprise portions of the topsheet 2, the backsheet 3 and the core 4 disposed between the topsheet 2 and the backsheet 3 while the intermediate peripheral wall section 6b comprises the portion of the backsheet 3 extending outward beyond the outer edge of the topsheet 2.

Along the first joining edges 10 and the second joining edges 12, portions of the topsheet 2 are folded inwardly of the panel 1 to be joining together and the portions of the backsheet 3 extending outward beyond the portions of the topsheet 2 are folded also inwardly of the panel 1 to be joined together.

Along the intermediate peripheral wall section 6b, the portion of the topsheet 2 extending transversely outward beyond the outer edge of the core 4 terminates immediately outside the outer edge of the core 4 while the portion of the backsheet 3 extends transversely outward beyond the outer edge of the topsheet 2.

The front and rear peripheral wall sections 6a, 6c cooperate with the bottom 5 to form a pocket P1 opening inward longitudinally of the panel 1, on one hand, and the intermediate peripheral wall sections 6b cooperate with the bottom 5 to form a pocket P2 opening inward transversely of the panel 1, on the other hand.

The peripheral wall 6 has a proximal end 6d extending at a level of the bottom 5 and a free end 6e extending at a level of the top opening 7 wherein a dimension L3 between the proximal end 6d and the free end 6e is uniform in all the front, rear and intermediate peripheral wall sections 6a, 6c, 6b. The dimension L3 is preferably in a range of 1~2 cm. The dimension L3 less than 1 cm would allow the body fluids to flow beyond the peripheral wall 6 and make a leak-barrier function of the peripheral wall 6 inadequate. The dimension L3 larger than 2 cm would cause the peripheral wall 6 to collapse inwardly of the panel 1 and to partially cover the upper surface of the bottom 5. Consequently, an exposed area of the bottom 5 would be unacceptably reduced to ensure a desired liquid-absorbent ability of the core 4.

Figure 5:
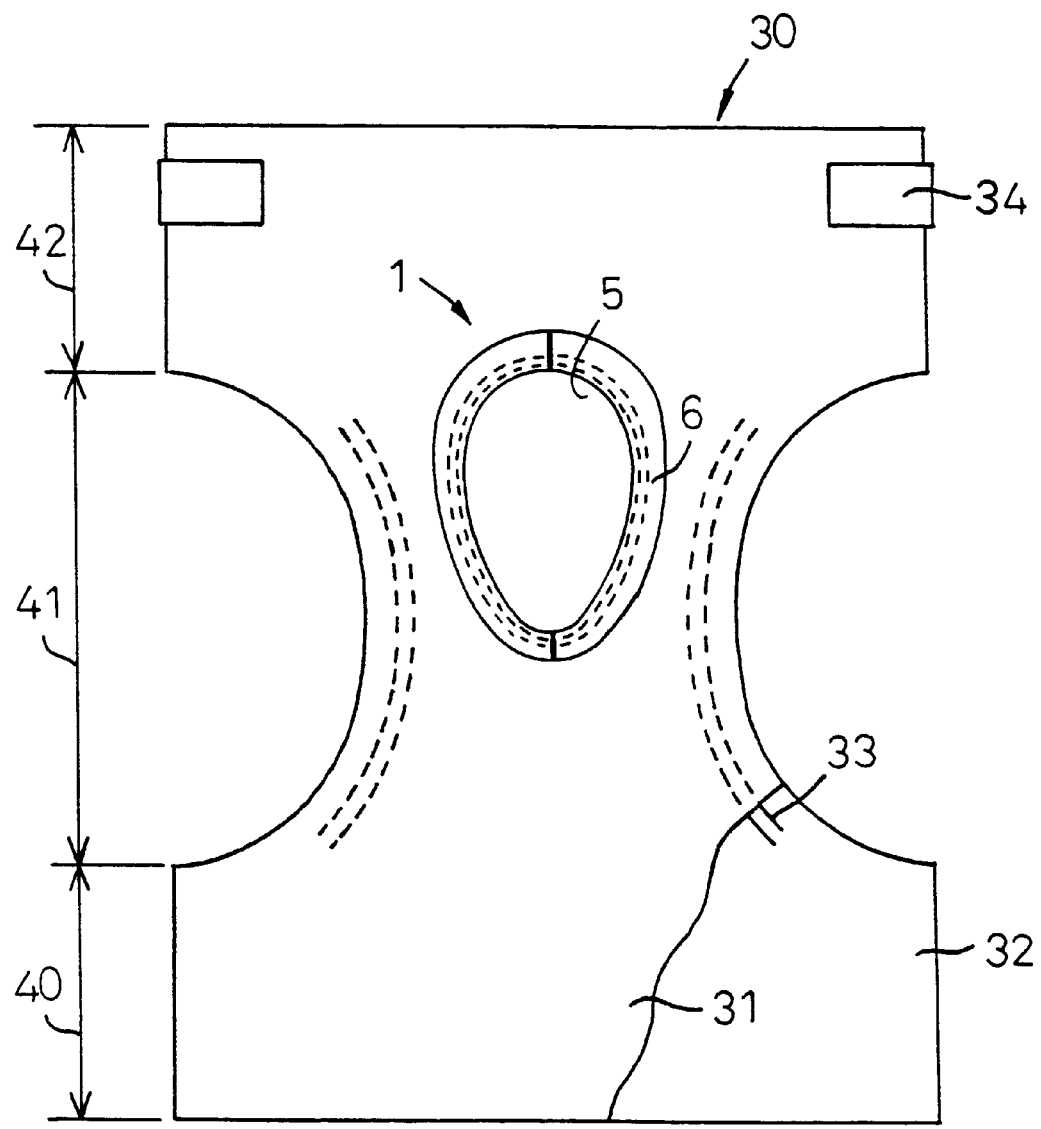
FIG. 5 is a partially cutaway plan view showing the panel attached to a diaper cover.

FIG. 5 is a partially cutaway plan view showing the panel 1 attached to a diaper cover 30. The diaper cover 30 is an hourglass-shaped laminate comprising a topsheet 31 made of plastic film and a backsheet 32 made of a nonwoven fabric. Longitudinally, the diaper cover 30 is composed of front and rear waist regions 40, 42 and a crotch region 41 extending between these front and rear waist regions 40, 42.

The crotch region 41 is provided along its transversely opposite side edges with elastic members 33 extending longitudinally of the cover 30 and are secured under tension to the inner surface of at least one of the topsheet 31 and the backsheet 32. The panel 1 is detachably attached to the inner surface of the cover 30 by means of suitable adhesive agent (not shown) so as to extend partially across the rear waist region 42 and the crotch region 41. Depending on a particular purpose to use the panel 1, a position at which the panel 1 is attached to the diaper cover 30 may be selected to obtain a function as a feces-receiving pad, a urine absorbent pad or a sanitary napkin.

The cover 30 is provided on transversely opposite side edges of its rear waist region 42 with tape fasteners 34 by means of which an assembly comprising the panel 1 and the cover 30 can be put on a wearer's body in the same manner in which the conventional disposable diaper is put on a wearer's body. For the particular purpose of use, the assembly should be put on the wearer's body with a substantially central zone of the panel's top opening 7 being opposed to the wearer's anus.

When the panel 1 is used for such purpose, body wastes are discharged directly into the top opening 7 without an apprehension that the cover 30 might be soiled with body wastes. The body wastes discharged onto the panel 1 can be easily disposed of by handling the relatively small panel 1 not by handling the relatively large cover 30. Preferably, the rear peripheral wall section 6c curved more acutely than the front peripheral wall section 6a is positioned in the crotch region 41 as the cover 30 is put on the wearer's body so that the rear end 22 may be smoothly received in the wearer's crotch without giving the wearer a feeling of discomfort due to use of the panel 1. The front peripheral wall section 6a curved more obtusely than the rear peripheral wall section 6c cooperating with the core 4 lying inside this section 6c can receive and absorb much amount of excretion. The dimension L3 between the proximal end 6d and the free end 6e of the peripheral wall 6 is substantially uniform in the front, rear and intermediate peripheral wall sections 6a, 6c, 6b and limited to a range of 1~2 cm. As a result, only the peripheral portion of the bottom 5 will be covered with the peripheral wall sections 6a, 6b, 6c even if these peripheral wall sections collapse toward the bottom 5. Thus, absorption of the body fluids by the bottom 5 of the panel 1 is not affected.

Figure 6:
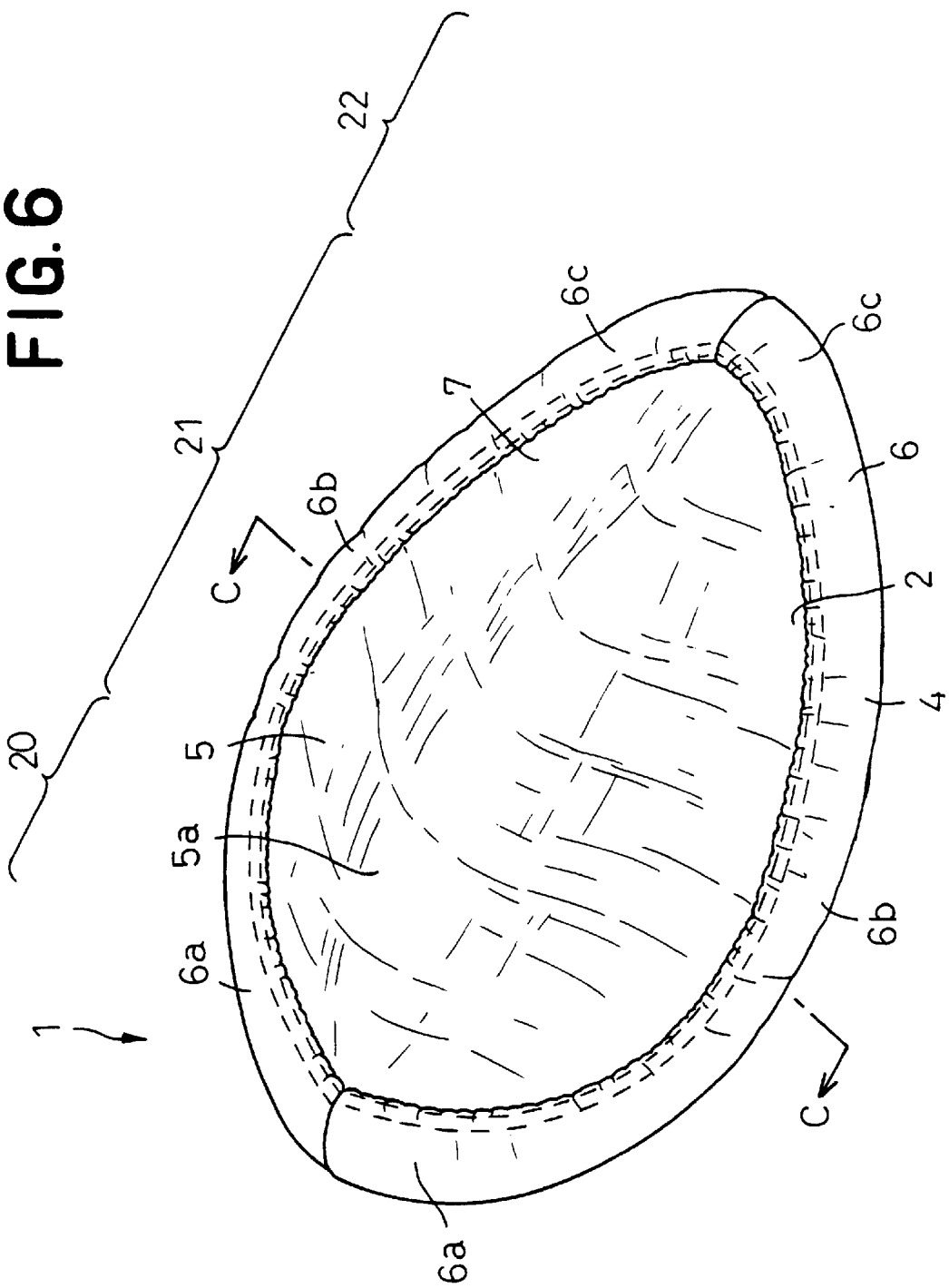
FIG. 6 is a partially cutaway view similar to FIG. 1 but showing an alternative embodiment.
Figure 7:
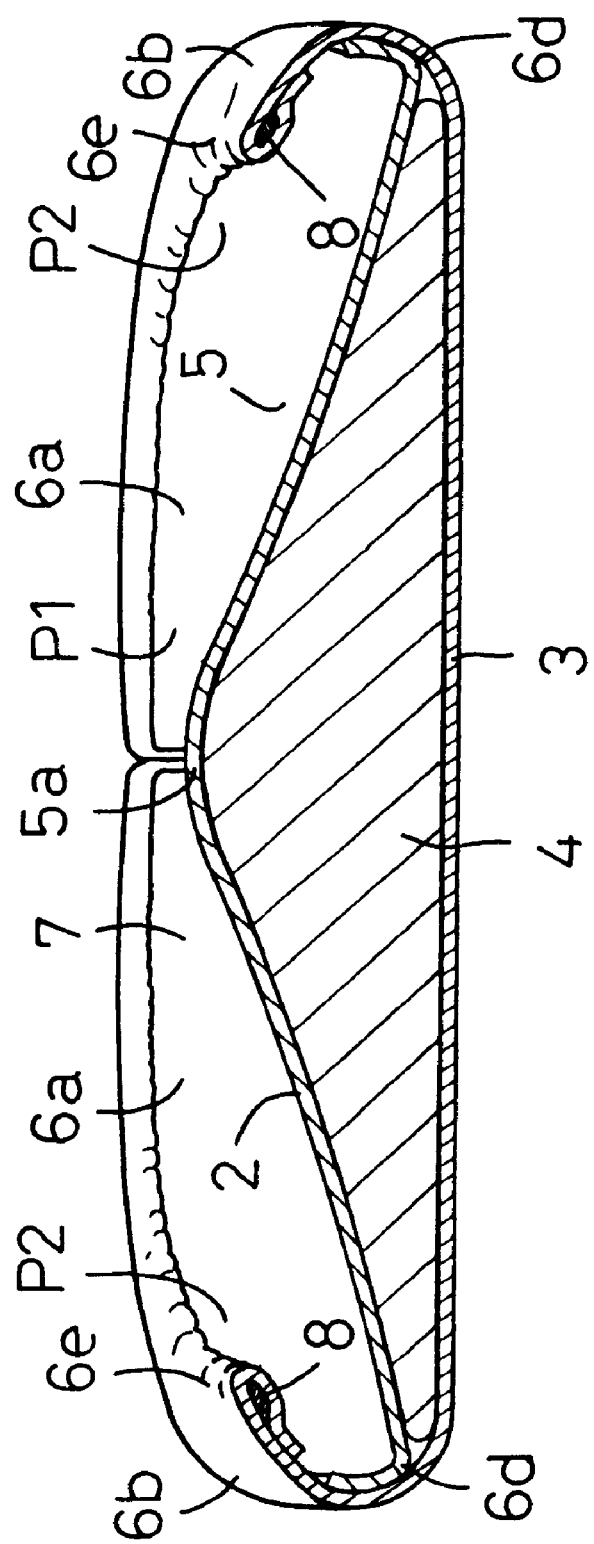
FIG. 7 is a sectional view taken along line C—C in FIG. 6.

FIGS. 6 and 7 are respectively a view similar to FIG. 1 but showing an alternative embodiment of this invention and a sectional view taken along line C—C in FIG. 6. The panel 1 according to this alternative embodiment is similar to the embodiment of FIG. 1 in that the panel 1 comprising the topsheet 2, the backsheet 3 and the core 4 disposed between these two sheets 2, 3 are longitudinally composed of the front region 20, the rear region 22 and the intermediate region 21 extending between the front and rear regions 20, 22 and contoured by the front and rear peripheral wall sections 6a, 6c in the front and rear regions 20, 22, respectively and the intermediate peripheral sections 6b in the intermediate region 21.

In the bottom 5 of the panel 1, the core 4 is gently convex upward along the center line Y to form a crest 5b extending longitudinally of the panel 1. When it is desired to use this panel 1 as a sanitary napkin, the crest 5b may be placed in close contact with a wearer's vaginal region to effectively absorb menstrual discharge. An amount exuding through the peripheral edge of the bottom 5 is reliably prevented by the peripheral wall 6 functioning as the barrier from leaking outward beyond the peripheral wall 6.

The topsheet 2 is formed by a liquid-pervious sheet such as a nonwoven fabric or a porous plastic film, preferably by a liquid-pervious but hydrophobic sheet. The backsheet 3 is formed by a liquid-impervious plastic film, a lamination of a plastic film and a hydrophobic nonwoven fabric, preferably by a breathable but liquid-impervious sheet.

The nonwoven fabric may be selected from a group including a spun lace nonwoven fabric, a needle punch nonwoven fabric, a melt blown nonwoven fabric, a thermal bond nonwoven fabric, a spun bond nonwoven fabric and a chemical bond nonwoven fabric. The nonwoven fabric preferably has a basis weight of 15~80 $g/m^2$, more preferably of 20~60 $g/m^2$. Component fibers of the nonwoven fabric may be selected from a group including polyolefine fiber, polyester fiber, polyamide fiber, and conjugated fiber of polyethylene/polypropyrene or polyester.

The core 4 is formed principally by a mixture of fluff pulp and highly absorptive hydrogel particles compressed and then covered with a water-pervious sheet such as tissue paper. Bonding of the sheets 2, 3 and attaching of the elastic members 8 may be carried out using a suitable adhesive agent or glue such as a hot melt adhesive agent or heat-sealing technique.

What is claimed is:

1. An article for dealing with body wastes comprising a laminated panel comprising a liquid-pervious topsheet, a liquid-impervious backsheet and a liquid-absorbent core disposed therebetween wherein said panel has a front region, a rear region and an intermediate region extending between said front and rear regions; wherein:

said panel has a bottom, a peripheral wall extending upward from a peripheral edge of said bottom and surrounding said peripheral edge of said bottom and a top opening defined by said peripheral wall; and said peripheral wall has an elastic stretchability along an edge of said top opening and comprising an obtusely curved front peripheral wall section contouring said front region, a rear peripheral wall section curved more acutely than said front peripheral contouring said rear region and a pair of intermediate peripheral wall sections describing circular arcs convex outward transversely of said panel so as to contour said intermediate region.

2. The article according to claim 1, wherein a peripheral length of said top opening is smaller than a length of the peripheral edge of said bottom.

3. The article according to claim 1, wherein said front peripheral wall section is formed by the steps of dividing, along a longitudinal center line of said panel, said front region defined by an outer edge progressively coming near to said center line in two divisions spaced from each other by a V-shaped notch opening forward longitudinally of said panel and drawing these two divisions nearer toward said center line until said two divisions are bonded along first bonding edges defined by respective legs of said V-shape on said center line Y; and said rear peripheral wall section is formed by the steps of dividing, along a longitudinal center line of said panel, said rear region defined by an outer edge progressively coming near to said center line in two divisions spaced from each other by an inverted V-shaped notch opening rearward longitudinally of said panel and drawing these two divisions nearer toward said center line until said two divisions are bonded along second bonding edges defined by respective legs of said inverted V-shape on said center line Y.

4. The article according to claim 3, wherein each of said first joining edges has the same length as each of said second joining edges and wherein said second joining edges include therebetween an angle larger than that included by said first joining edges.

5. The article according to claim 1, wherein said peripheral wall comprises a proximal end lying at a level of said bottom and a free end lying at a level of said opening; wherein a dimension between said proximal end and said free end is in a range of 1~2 cm; and wherein said dimension is uniform in all said front, rear and intermediate wall sections.

6. The article according to claim 1, wherein at least one of said front peripheral wall section and said rear peripheral wall section comprises a portion of said topsheet, a portion of said backsheet and a portion of said core disposed between these two sheets and wherein said intermediate peripheral wall sections comprise at least portions of said backsheet.

7. The article according to claim 1, wherein said bottom comprises said topsheet, said backsheet and said core is gently convex upward along said center line to form a crest extending longitudinally of panel in vicinity of said center line.

8. The article according to claim 1, wherein said article is an absorbent pad adapted to be attached to an inner surface of a diaper cover.

* * * * *